(12) United States Patent
Muhs et al.

(10) Patent No.: US 6,603,069 B1
(45) Date of Patent: Aug. 5, 2003

(54) ADAPTIVE, FULL-SPECTRUM SOLAR ENERGY SYSTEM

(75) Inventors: Jeffrey D. Muhs, Lenoir City, TN (US); Dennis D. Earl, Knoxville, TN (US)

(73) Assignee: UT-Battelle, LLC, Oak Ridge, TN (US)

(*) Notice: Subject to any disclaimer, the term of this patent is extended or adjusted under 35 U.S.C. 154(b) by 9 days.

(21) Appl. No.: 09/953,848

(22) Filed: Sep. 18, 2001

(51) Int. Cl.$^7$ .......................... H01L 31/052; C12M 1/00
(52) U.S. Cl. ...................... 136/246; 136/253; 136/291; 136/248; 435/292.1; 250/227.11; 126/683; 126/685; 126/690; 385/900; 60/641.8
(58) Field of Search ................................ 136/246, 253, 136/291, 248; 435/292.1; 250/227.11; 126/683, 685, 690; 385/900; 60/641.8

(56) References Cited

U.S. PATENT DOCUMENTS

| | | |
|---|---|---|
| 4,297,000 A | 10/1981 | Fries |
| 4,328,389 A | 5/1982 | Stern et al. |
| 4,525,031 A | 6/1985 | Mori |
| 4,539,625 A | 9/1985 | Bornstein et al. |
| 4,626,065 A | 12/1986 | Mori |
| 4,700,013 A | 10/1987 | Soule |
| 4,970,166 A * | 11/1990 | Mori ...................... 435/292.1 |
| 5,371,660 A | 12/1994 | Levens |
| 5,575,860 A | 11/1996 | Cherney |
| 5,614,378 A * | 3/1997 | Yang et al. .............. 435/257.1 |
| 5,658,448 A | 8/1997 | Lasich |
| 5,716,442 A | 2/1998 | Fertig |
| 6,128,135 A | 10/2000 | Stiles et al. |

FOREIGN PATENT DOCUMENTS

| | | |
|---|---|---|
| DE | 19016 A2 | 11/1980 |
| DE | 19705046 A1 | 2/1998 |
| EP | 0922914 A2 | 6/1999 |
| GB | 2 029 883 A | 3/1980 |
| JP | 57-181689 A | 11/1982 |
| JP | 61-139382 A | 6/1986 |
| JP | 4-84883 A | 3/1992 |
| JP | 5-64577 A | 3/1993 |
| JP | 8-200839 A | 8/1996 |
| JP | 8-329712 A | 12/1996 |

OTHER PUBLICATIONS

"Applications for Hybrid Lighting System" at http://www.ornl.gov/hybridlighting/applications.htm, last revision Feb. 6, 2002.*

Jeff Muhs, "Design and Analysis of Hybrid Solar Lighting and Full–Spectrum Solar Energy Systems," American Solar Energy Society's Solar2000 Conference, ASME, (Jun. 16, 2000).

D. D. Earl et al, "Preliminary Results on Luminaire Designs for Hybrid Solar Lighting Systems," Proceedings of Forum 2001: Solar Energy:The Power to Choose, ASME, (Apr. 21, 2001).

* cited by examiner

*Primary Examiner*—Alan Diamond
(74) *Attorney, Agent, or Firm*—Kirk A. Wilson

(57) ABSTRACT

An adaptive full spectrum solar energy system having at least one hybrid solar concentrator, at least one hybrid luminaire, at least one hybrid photobioreactor, and a light distribution system operably connected to each hybrid solar concentrator, each hybrid luminaire, and each hybrid photobioreactor. A lighting control system operates each component.

9 Claims, 10 Drawing Sheets

Hybrid Solar Bioreactor

Hybrid Solar Concentrator

Hybrid Solar Bioreactor

Hybrid Solar Concentrator

| System Performance | |
|---|---|
| Loss Parameter | Transmission |
| Primary Mirror | 92% |
| Secondary Mirror | 94% |
| Collection losses | 97% |
| Fresnel losses | 94% |
| Fiber attenuation (@ 6 meters) | 78% |
| Fresnel losses | 94% |
| Luminaire losses | 85% |
| Total | 50% |

ADAPTIVE, FULL-SPECTRUM SOLAR ENERGY SYSTEM

FEDERAL RESEARCH STATEMENT

This invention was made with Government support under contract no. DE-AC05-00OR22725 to UT-Battelle, LLC, awarded by the United States Department of Energy. The Government has certain rights in the invention.

BACKGROUND OF INVENTION

Throughout the 1900"s, use of the sun as a source of energy has evolved considerably. Early in the century, the sun was the primary source of interior light for buildings during the day. Eventually, however, the cost, convenience, and performance of electric lamps improved and the sun was displaced as our primary method of lighting building interiors. This, in turn, revolutionized the way we design buildings, particularly commercial buildings, making them minimally dependent on natural daylight. As a result, lighting now represents the single largest consumer of electricity in commercial buildings.

During and after the oil embargo of the 1970s, renewed interest in using solar energy emerged with advancements in daylighting systems, hot water heaters, photovoltaics, etc. Today, daylighting approaches are designed to overcome earlier shortcomings related to glare, spatial and temporal variability, difficulty of spatial control and excessive illuminance. In doing so, however, they waste a significant portion of the visible light that is available by shading, attenuating, and or diffusing the dominant portion of daylight, i.e., direct sunlight which represents over 80% of the light reaching the earth on a typical day. Further, they do not use the remaining half of energy resident in the solar spectrum (mainly infrared radiation between 0.7 and 1.8 um), add to building heat gain, require significant architectural modifications, and are not easily reconfigured. Previous attempts to use sunlight directly for interior lighting via fresnel lenes collectors, reflective light-pipes, and fiber-optic bundles have been plagued by significant losses in the collection and distribution system, ineffective use of nonvisible solar radiation, and a lack of integration with collocated electric lighting systems required to supplement solar lighting on cloudy days and at night.

Similar deficiencies exist in photovoltaics, solar thermal electric systems, and solar hot water heaters. FIG. 2 shows the conversion efficiency of traditional silicon-based solar cells in the ultraviolet and short wavelength visible region of the solar spectrum is low and the solar energy residing beyond ~1.1 um is essentially wasted. To overcome this and address other economic barriers, one approach has been to develop utility-scale photovoltaic (PV) and solar thermal concentrators. The rationale being that the cell area and, consequently, the cell cost can be reduced by approximately the same amount as the desired concentration ratio. Unfortunately, this cost-savings is typically offset by the added cost and complexity of the required solar concentrator and tracking system.

In recent years, researchers have begun developing photobioreactors that use sunlight-induced photosynthesis to sequester carbon to produce biofuels such as hydrogen using cyanobacteria. Large-scale photobioreactors are already indispensable in the successful commercial production of phototrophic unicellular algae valued in such markets as aquaculture, pharmaceuticals, animal-feed additives and health foods. Unfortunately, very little of the incident sunlight is tapped to maximize cyanobacteria growth rates, and only 10% of the energy residing in the visible portion of the spectrum is typically used productively to produce biomass. Terrestrial solar radiation can reach ~2000 $\mu E$ $m^2$ $s^{-1}$, which easily satisfies the photosynthetic photon flux (PPF) requirements of algae. Indeed, at elevated PPF levels (greater than ~200 $\mu E$ $m^2$ $s^{-1}$), the kinetic imbalance between the rate of photon excitation and thermally-activated electron transport results in saturation of the photosynthetic rate. In the case of thermophilic and mesophilic cyanobacteria that are ideally-suited for carbon sequestration because of their thermal adaptation to higher temperatures, even a lower PPF level (~6 100 $uEm^2s^{-1}$) is required to achieve maximum carbon fixation. Thus, most of the lighting energy available from solar irradiance goes unused.

The principal hurdle to the scale up of photobioreactors to achieve a viable commercial-scale production of algae is lighting limitation, both in terms of light delivery and distribution and energy expenditure. For instance, current methods for mass cultivation of marine microalgae include translucent fiberglass cylinders, polyethylene bags, carboys and tanks under artificial lighting or natural illumination in greenhouses. In these cases, however, at an algal density of 0.45 g/L, for example, light penetrates the suspension only to a depth of 5 cm, leaving a significant percentage of the cells in complete darkness at any given time. As such, microalgal production in these systems seldom exceeds 100 kg DW per year per facility, and maintaining these systems is labor- and space-intensive and quite unreliable. Moreover, when lighting is provided by artificial lamps (such as fluorescent, high-pressure sodium or incandescent) in close proximity to the bioreactor vessel, the comparatively poor luminous efficacy and dissipation of heat from the lamps present a constant problem.

Natural bioreactors using traditional raceway cultivators commonly waste 90 to 95% of the incident photosynthetic photon flux at high algal densities along with the remaining solar energy resident in the UV and IR portion of the spectrum. This equates to an overall solar energy utilization factor of 2.5 to 5%, making conventional photobioreactors very difficult to justify from a cost and performance perspective.

The approach first demonstrated in Japan to improve the sunlight utilization efficiency of natural photobioreactors is to collect, transport, and distribute sunlight over a larger surface area, thereby improving the sunlight utilization efficiency by reducing losses caused by saturation. The concept included the use of the earlier-mentioned fresnel-lens sunlight collector and a fiber optic bundle system to transport and distribute the light. Losses in the visible-light collection, transport and distribution system were typically more than 75%, and the 2x-to-3x improvements in sunlight utilization was far outweighed by the added cost ($5,000/$m^2$ of sunlight collected). This approach serves as partial precursor to this invention.

SUMMARY OF INVENTION

This invention improves the total end-use power displacement efficiency of solar energy by integrating solar technologies into multi-use hybrid systems that better utilize the entire solar energy spectrum. As illustrated in FIG. 3, a primary mirror concentrates the entire solar spectrum onto a secondary optical element where the visible portion of the solar spectrum is separated from the UV and near infrared portions. The two energy streams are used for different purposes, i.e. lighting and electricity generation or process heat.

This adaptive, full-spectrum (AFS) solar energy system is a unique alternative to solar energy use in buildings and photosynthetic-based bioreactors. It uses solar energy from a dynamic, systems-level perspective, integrates multiple interdependent technologies, and makes better use of the entire solar energy spectrum on a real-time basis.

The solar system uses a hybrid solar concentrator, shown in FIG. 3, that efficiently collects, separates, and distributes the visible portion of sunlight while simultaneously generating electricity from the infrared portion of the spectrum using new gallium antimonide (GaSb) infrared thermophotovoltaics (IR-TPVs). The optical and mechanical properties of improved large-core polymer optical fibers more efficiently deliver large quantities of visible sunlight into buildings and photobioreactors. Once delivered, the visible sunlight is used much more effectively than previously to illuminate building interiors using new hybrid luminaires. Improved cyanobacteria growth rates, packing densities, and solar utilization efficiencies in hybrid solar photobioreactors that use fibers to more efficiently distribute and use light that would have otherwise been wasted via photosynthetic saturation is also provided.

This invention redirects and more-efficiently uses portions of the solar energy spectrum originating from a common two-axis, tracking solar concentrator in real-time using electro-optic and or opto-mechanical devices. Analytical/experimental models and intelligent control strategies enhance the use of adaptive full-spectrum solar energy systems in its two primary applications i.e. commercial buildings (also illustrated in FIG. 1) and hybrid solar photobioreactors used to mitigate $CO_2$ at power plants (also illustrated in FIG. 1).

This invention uses: a) advanced materials including GaSb thermophotovoltaics, and spectrally-selective UV cold mirror thin film coatings, b) biomass resource development through innovative approaches to improve sunlight utilization in photobioreactors used in carbon sequestration and the production of fuels, chemicals, and agriculture products, c) intelligentsensor/control systems for use in adaptive solar energy systems in commercial buildings, d) computational science tools to aid in the design of adaptive full-spectrum solar energy systems, model application-specific dynamic system behavior, and predict/optimize performance, and e) distributed power conversion systems for use in buildings and new hybrid solar photobioreactors.

DETAILED DESCRIPTION

Figure 1:
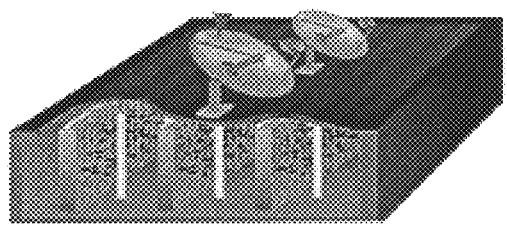
FIG. 1 shows the major components of the adaptive, full-spectrum (AFS) solar energy system.
Figure 1:
Figure 1:
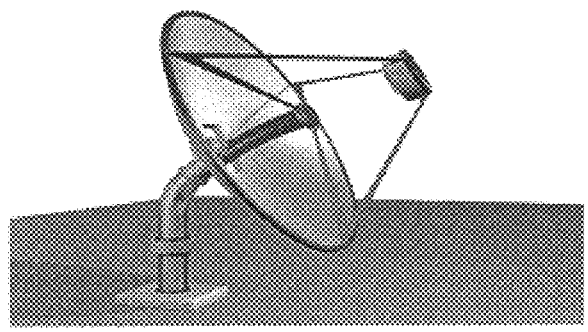
Figure 1:
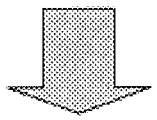
Figure 1:
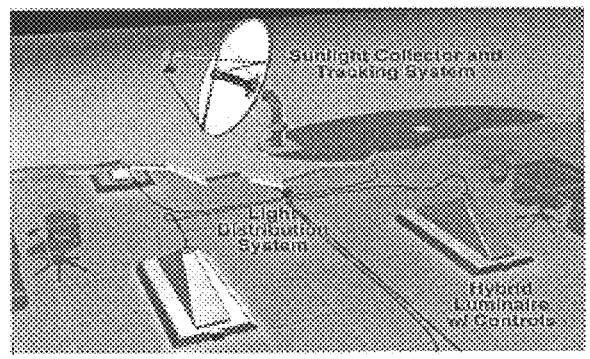
Figure 2:
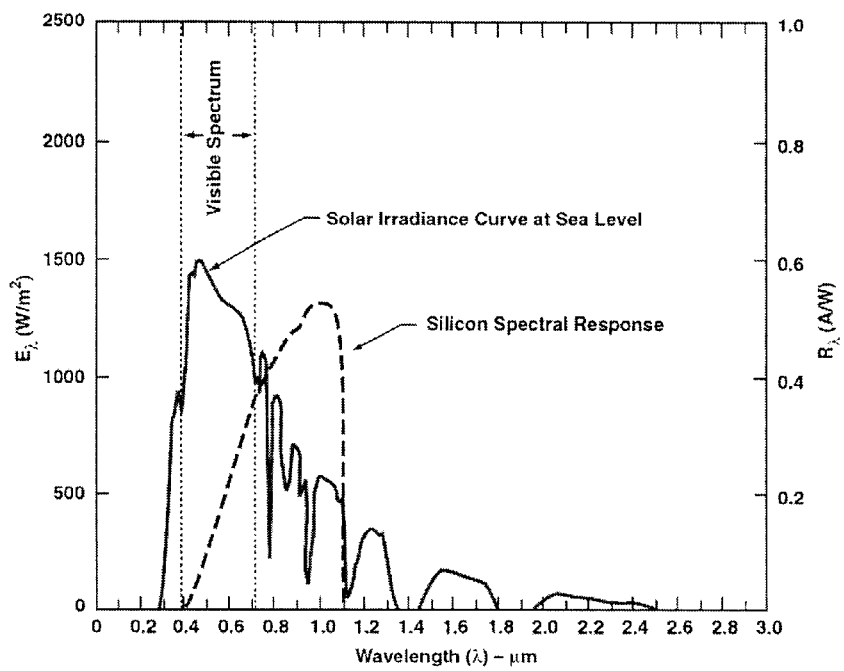
FIG. 2 is the approximate spectral radiance of the sun at mean earth-sun separation and associated silicon spectral response.
Figure 3:
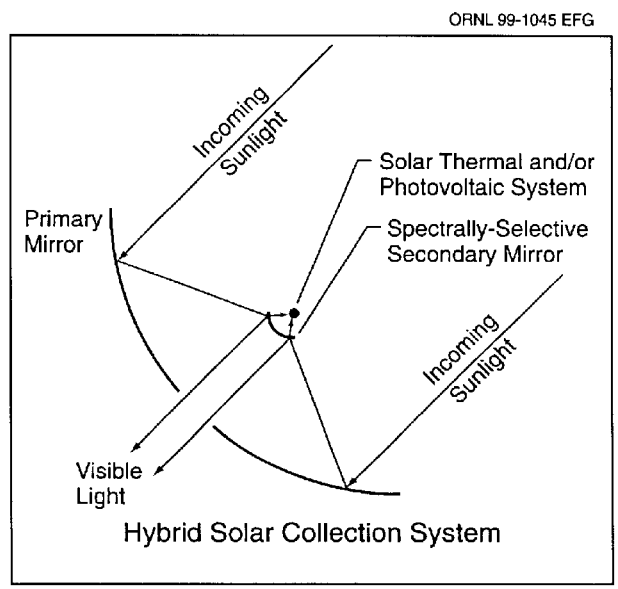
FIG. 3 shows a schematic representation of hybrid solar concentrator.
Figure 4:
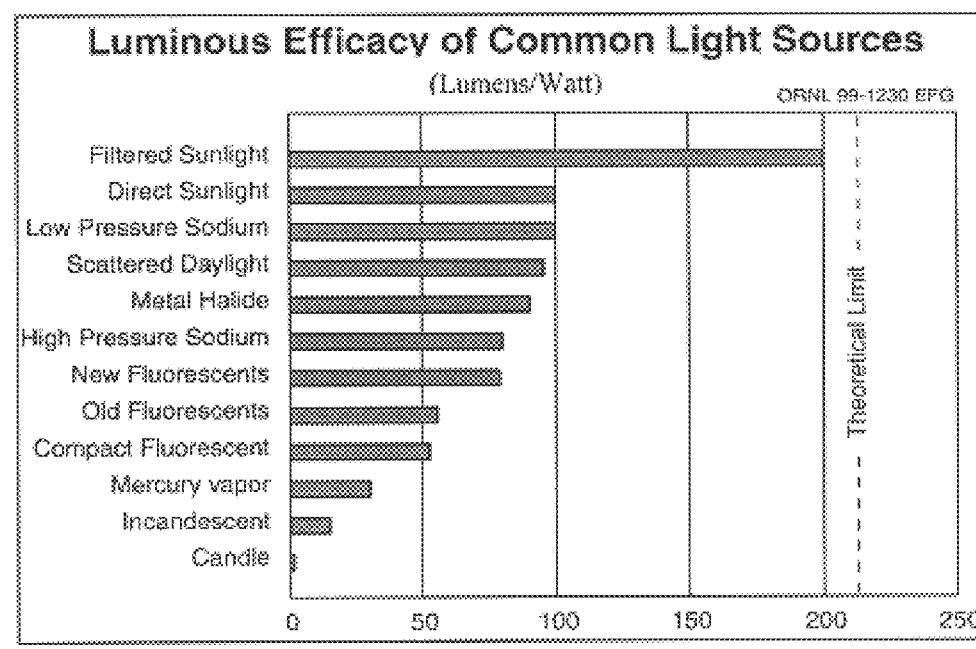
FIG. 4 is the luminous efficacy of common light sources.

The adaptive, full-spectrum (AFS) solar energy system takes advantage of the fact that new GaSb IR-TPV very efficiently convert concentrated energy residing in the near-IR solar spectrum between 0.7 and 1.8 um at a conversion efficiency of ~23%. Similarly, the visible portion of sunlight is inherently more efficient when used directly for lighting. The luminous efficacy of direct sunlight is 90 to 100 lumens/Watt (lm/W) depending on the sun"s orientation relative to the earth, atmospheric conditions, etc. The luminous efficacy of filtered sunlight (180 200 lm/W) far exceeds existing electric lamps (15 90 lm/W). Unlike most comparisons with nonrenewable alternatives, the luminous efficacy of filtered sunlight is more than double its only competition (electric lamps), see FIG. 4. Therein lies the primary motivation for using filtered sunlight for lighting purposes in buildings and photobioreactors while using the remaining IR energy for electricity generation.

Figure 5:
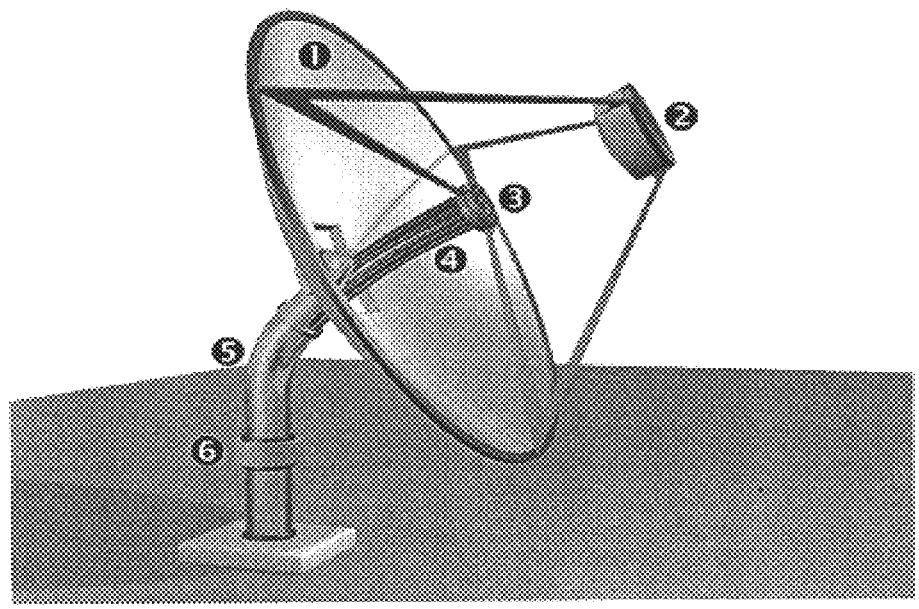
FIG. 5 shows the components of the hybrid solar concentrator.
Figure 6:
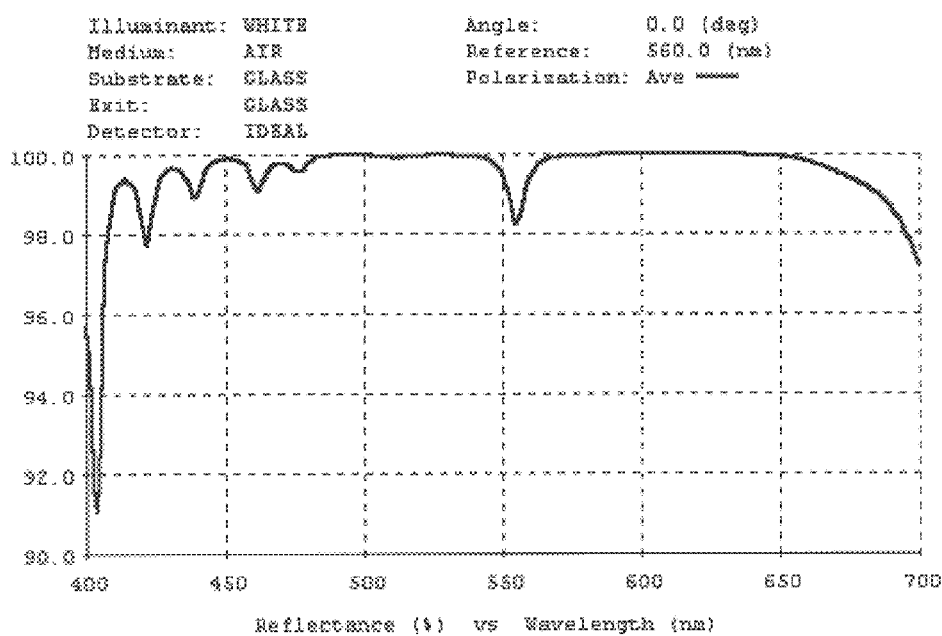
FIG. 6 is a graph of the spectral response of the sputtered UV cold mirror.
Figure 7:
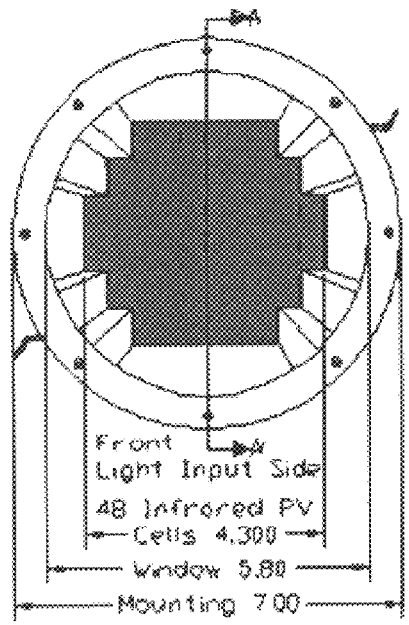
FIG. 7 is a front view of the IR-TPV.
Figure 8:
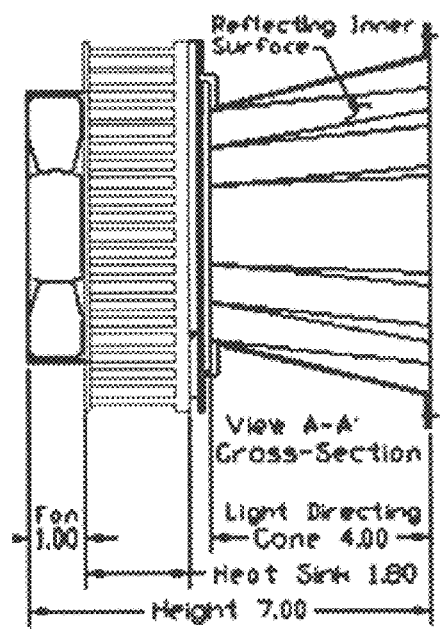
FIG. 8 is a section cut A—A of the IR-TPV showing the cooling fan.

FIG. 5 illustrates the preferred embodiment of the hybrid solar concentrator that takes advantage of the above strategy for both applications. A 1.6 m diameter primary mirror 1 is fabricated using formed glass and a second surface reflective coating that concentrates 2 $m^2$ of sunlight onto a 25 cm diameter secondary optical element 2 consisting of a faceted, high temperature glass substrate sectioned into 12 or more surfaces each of which is shaped to reflect visible light onto large-core optical fibers using a sputtered UV cold mirror coating having a spectral response, as shown in FIG. 6. The secondary optical element 2 also includes a nonimaging optic concentrator that uniformly distributes IR radiation onto a IR-TPV with an accompanying self-power cooling fan, as shown in FIG. 8. A concentric fiber mount assembly 3 contains 12 or more large-core optical fibers 4, each fiber 5 to 12 mm in diameter. An angled, hollow rotating assembly 5 reduces the range of motion required for altitude tracking by the conventional azimuth rotational tracking mechanism 6.

Figure 16:
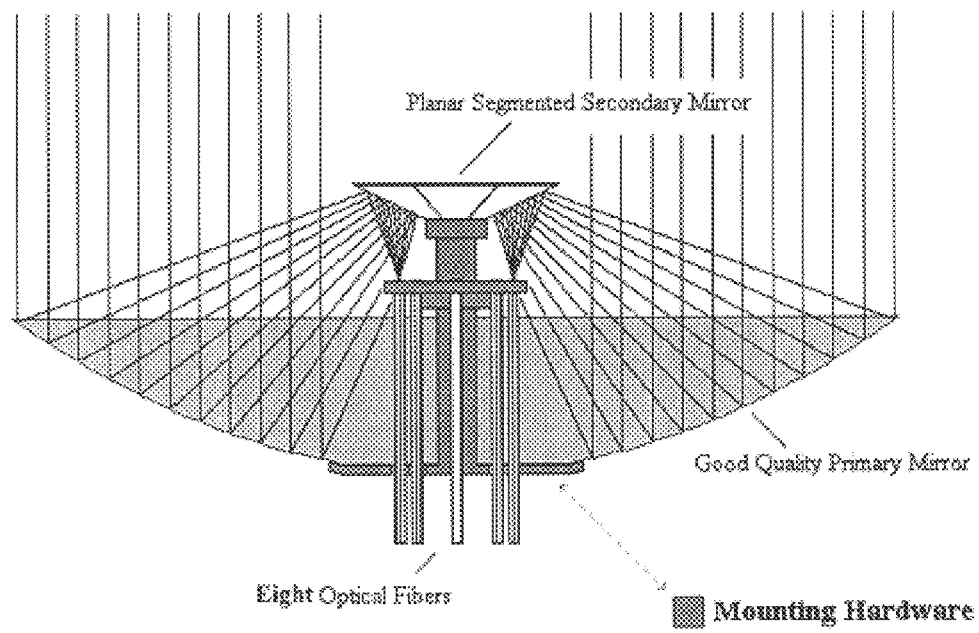
FIG. 16 shows a first embodiment of the hybrid solar concentrator.
Figure 17:
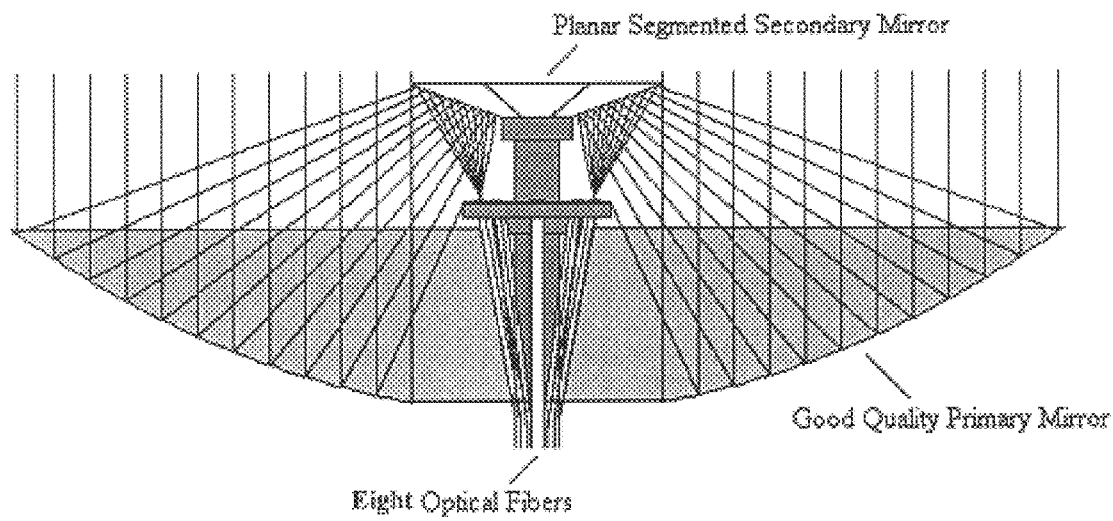
FIG. 17 shows a modified first embodiment of the hybrid solar concentrator.

Other embodiments of the hybrid solar concentrator include a first concentrator embodiment, as shown in FIG. 16, which utilizes a good-quality 1.1 m diameter glass primary mirror and segmented planar secondary optical element to precisely focus light into eight large core optical fibers. A modified first embodiment, which orients the optical fibers at a slight angle for improved efficiency, is shown in FIG. 17. The second concentrator embodiment again utilizes a good-quality 1.1 m diameter glass primary mirror but uses an elliptical secondary optical element. The elliptical secondary element extends the focus of the primary mirror and couples light into a packed array of nine optical fibers. The third concentrator embodiment represents a lower cost solution and uses a low quality coated 1.5 m diameter hydroformed satellite dish as the primary mirror. An elliptical secondary element refocuses the light onto a packed array of 9 optical fibers.

The first concentrator embodiment uses a high quality parabolic primary mirror with a segmented secondary optical element to precisely split and focus incident solar radiation into eight large-core optical fibers. The system is designed to couple a maximum of 10,000 lumens into each optical fiber with a high total system efficiency in the visible portion of the spectrum. Collimated light from the sun is collected and focused using a good quality parabolic primary mirror. The focused light is split and redirected toward eight large-core optical fibers mounted to a center post. The mounting hardware does obscure some of the light focused by the primary mirror and will result in less than optimal efficiency for this design. This reduction in optical efficiency was necessary to meet the mechanical requirements that all fibers fit into a 4" post after exiting the backside of the primary mirror.

The first embodiment uses a 46.5" diameter parabolic mirror with a focal length of 16.5", as manufactured by ROC glassworks, to serve as the primary mirror. The glass mirror, with front-surface coating, was fabricated using a "glass bending" technique that provided a good quality optical surface at a reasonable price. A 12" hole was bored in the center of the mirror to permit future mounting of a secondary mirror and fiber optic holding apparatus. The mirror was coated, by FLABEG Inc., with an enhanced aluminum coating. The coating provides high reflectivity across the visible spectrum and is a durable coating suitable for the environmental conditions expected. On a cloudless day, 1.0 $m^2$ of sunlight delivers an average of 1000 Watts of optical power. Of that, 490 watts lies in the visible portion of the spectrum. The area of the primary mirror (assuming no center hole) of the first embodiment is approximately 1.096 $m^2$, giving a maximum theoretical collection energy of 537 Watts. Simulations predict that the first embodiment mirror will collect only 458 Watts. The efficiency of the primary mirror, having considering surface aberrations, scattering losses, coating losses, and center bore hole loss, is approximately 85.2%.

The purpose of the secondary optical element is two fold. First, the secondary element must function to redirect focused light toward multiple large core optical fibers and, second, it should separate out non-visible light for use in photovoltaic conversion. To redirect the light focused by the previously described primary, a segmented secondary element was used. The mirror in the element utilizes a cold mirror coating to efficiently separate the infrared and visible portions of the spectrum. The HeatBuster®cold mirror coating, developed by Deposition Sciences Inc., is a typical cold mirror coating that reflects UV and visible light while transmitting IR. Using a MicroDyn sputtering technique allows the coating to operate up to a maximum temperature of 500° C. This high temperature capability is necessary since it is anticipated that the secondary element may absorb significant levels of heat.

Using an initial input energy of 537 Watts (which corresponds to the maximum possible power of visible solar light falling within a 46.5" diameter space), the total amount of light focused on the optical fiber plane is 381 Watts. This corresponds to a total concentrator efficiency of 70.9% and includes the coating losses in the primary and secondary, center hole losses in the primary, obscuration of the beam path by the fiber optic holder apparatus, and surface deviations/scattering losses in the primary. Fresnel losses at the optical fiber interface are not included.

The modified first embodiment (FIG. 17) also has a segmented planar secondary element used to redirect the light focused by the primary mirror, but is modified for use with optical fibers tilted at 10°. The redirected focus is located 95.0 mm from the base of the secondary mirror, in the optical fiber plane. The fiber optic holder is modified slightly to accommodate the 10° tilt in the optical fiber along with a small spacing between optical fibers.

Using an initial input energy of 537 Watts (which corresponds to the maximum possible power of visible solar light falling within a 46.5" diameter space), the total amount of light focused on the optical fiber plane (for the modified first embodiment) is 407 Watts. This corresponds to a total concentrator efficiency of 75.9% and includes the coating losses in the primary and secondary, center hole losses in the primary, obscuration of the beam path by the fiber optic holder apparatus, and surface deviations/scattering losses in the primary. Fresnel losses at the optical fiber interface are not included.

Figure 9:
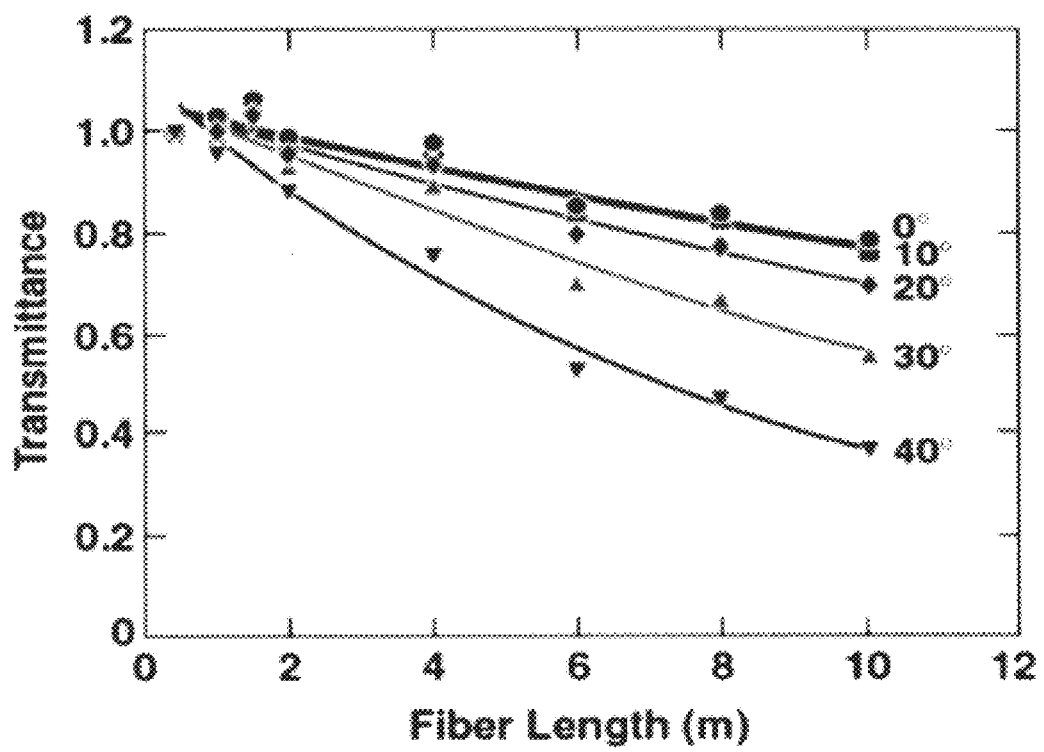
FIG. 9 is the end-to-end attenuation in large-core optical fibers at various incident angles.

For building applications, the most significant loss factor in the light collection and distribution system is the end-to-end attenuation in large-core optical fibers (see FIG. 9). This invention more efficiently and cost-effectively transports sunlight through new polymer-based large-core optical fibers rather than glass fiber optic bundles. A new "hybrid" luminaire, illustrated in FIG. 10, spatially distributes both fiberoptic-delivered sunlight and electric light in a general lighting application and controlling the relative intensity of each based on sunlight availability using photosensors and dimmable electronic ballasts. Thus, natural light is collected at a central location and distributed to multiple luminaires.

A major step toward the realization of using fiber optic transported solar light for internal lighting purposes involves the development of a hybrid luminaire to seamlessly balance lamp and fiber optic transported solar illuminants. Fluctuations in the intensity of collected solar light, due to changing cloud coverage or solar collector movement, requires rapid compensation by electric lamps to maintain a constant room illumination. If the spatial intensity distribution of a hybrid luminaire"s electric lamp does not closely match the spatial intensity distribution of the luminaire"s fiber optic end-emitted solar illuminant, then the shift between artificial and solar lighting will be noticeable to the occupant and is highly undesirable.

Figure 10:
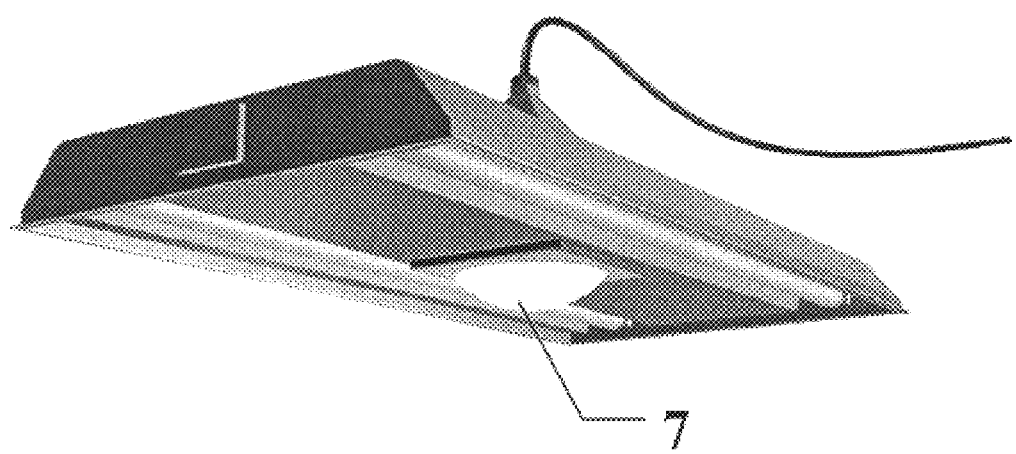
FIG. 10 is the hybrid luminaire rendering.
Figure 18:
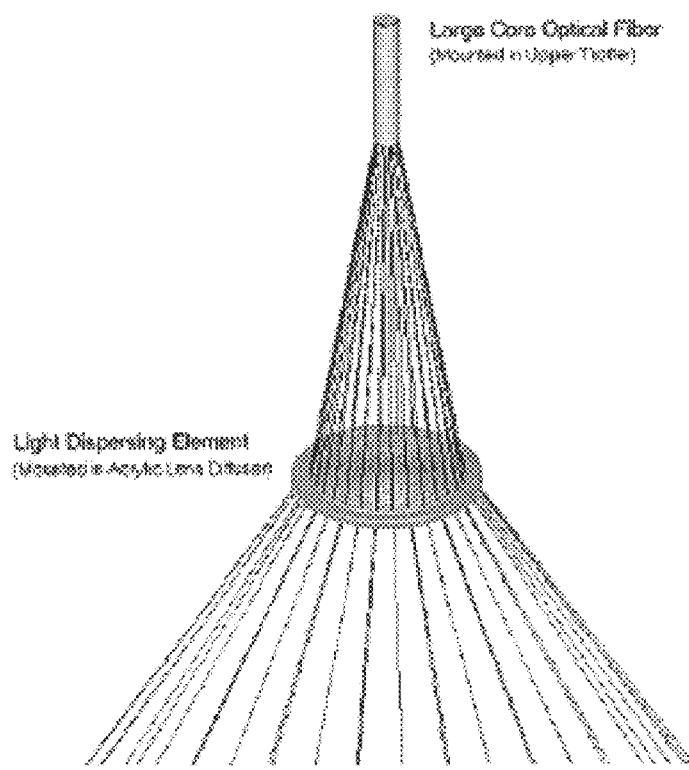
FIG. 18 shows a typical light dispersing element and optical fiber for the hybrid luminaires.

A four-tube Lithonia GT8 troffer, as rendered in FIG. 10, equipped with a #19 pattern 4.0 mm acrylic lens diffuser, was modified to include two 15 cm diameter light dispersing elements 7 which utilize micro-optic structures. FIG. 10 shows only one light dispersing element 7. The two 4.0 mm thick light dispersing elements are mounted within the fixture"s acrylic lens diffuser and allow a range of highly divergent quasi-elliptical spatial intensity distributions to be generated from two circular fiber optic end-emitting sources fed through the top surface of the fixture's troffer. Variations in the spatial intensity distribution of the dispersed solar light can be made without the need to readjust the alignment or spacing between the optical fiber and the light dispersing element 7, as shown in FIG. 18. A static configuration is maintained.

The optical efficiency of the light dispersing elements has been estimated at greater than 90% while the optical efficiency of the original luminaire is reduced by 3%, from 76% to 73%. To improve the matching between the electric and solar spatial intensity distributions, the number of elements can be increased to four or even eight. However, increasing the number of light dispersing elements 7 reduces the optical efficiency of the fixture and results in higher costs.

A second embodiment of the hybrid luminaire comprised a cylindrical diffusing rod having a 2.54 cm diameter, 1.0 m long, optically clear cylinder with a polished lower hemisphere and a diffuse upper hemisphere. Light launched from a butt-coupled optical fiber, scatters from the diffuse upper surface of the cylinder and escapes through the polished lower surface of the cylinder. To improve efficiency, upward-scattered light is redirected back toward the lower hemisphere of the diffusing rod with a silver-coating on the upper hemisphere.

Three diffusing rods, each placed mid-way and slightly above adjacent fluorescent lamps in a 4-tube PARAMAX® Parabolic Troffer with 24-cell louvre baffle, were expected to produce a spatial intensity distribution which closely matched that of the four fluorescent tubes. However, initial modeling of the diffusing rod indicated that the intensity of the scattered light was too highly concentrated toward one end of the rod, creating uneven illumination. In addition, a large portion of the light entering the diffusing rod at small angles was not being scattered at all and, instead, was merely being reflected from the planar end of the diffusing rod back into the butt-coupled optical fiber. To overcome these deficiencies, a silver-coated concave mirror surface at the end of the rod was added to the diffusing rod model. This concave end-mirror strongly diverged low-angle incident light, hence improving the optical efficiency of the diffusing rod while also improving the overall uniformity of the scattered light. To further improve the uniformity of the scattered light, a 40 cm strip along the center of the diffusing rod"s top hemisphere was modeled with a larger scattering fraction than the outer ends to increase the amount of scattered light emitted from the center of the diffusing rod.

Simulations of the spatial intensity distribution resulting from the fluorescent lamps and/or the diffusing rods revealed only minor differences between the two distributions, and only minor deviation from the fixture"s original spatial intensity distribution. However, due to obstruction and scattering losses associated with the inclusion of the three diffusing rods, the optical efficiency of the fixture was decreased from 64% to 53%. The diffusing rod itself was estimated to be only 50% efficient at converting a fiber optic end-emitted source into a cylindrical source. This efficiency was strongly dependent upon the intensity profile of the fiber optic end-emitted light and the combination of scattering values used along the top surface of the diffusing rod.

The cylindrical diffusing rod was a 2.54 cm diameter, 1 m long, cast acrylic rod, with high optical clarity and optically smooth outer surface. The rod was diamond-machined on one end to create a concave surface with a radius of curvature of 4.0 cm, and polished on the other end to create a planar optical surface suitable for butt-coupling to a large-core optical fiber. The top hemisphere of the rod was sandblasted to produce a uniform scattering surface and both the top hemisphere and concave end-mirror were coated with aluminum. Due to construction limitations, the top surface did not exhibit a variable surface scatter as originally modeled.

Preliminary testing of the cylindrical diffusing rod revealed a discrepancy between the desired modeled surface scatter and the actual surface scatter created by the sandblasting technique. Because optical scattering is often difficult to accurately premodel in software, the result was not entirely unexpected. The actual surface scatter created by the sandblasting technique was much larger than modeled and created a diffusing rod with an uneven illumination. However, now given the correlation between the modeled scattering values and the actual scattering values, it is possible to re-simulate and re-design the cylindrical diffusing rod to emit a more uniform intensity distribution. Additional factors related to optical efficiency and construction costs are currently being evaluated.

In the hybrid solar photobioreactors, large-core optical fibers are used to transport light into growth chambers and once inside, function as a distributed light source (much like fluorescent lamps) to illuminate cyanobacteria. New fiber configurations specifically-designed to optimize the side-lighting efficiency of large-core optical fibers are used, improving upon the cost and performance of fiber optic bundle sidelighting designs developed in the 1980s. The improved illumination design configurations of the photobioreactor: a) takes advantage of improved sidelighting, b) increases the surface area illuminated, c) drastically reduces photosynthetic saturation, d) demonstrates the ability to achieve much higher volumetric carbon fixation rates, e) filters unwanted UV and IR radiation from the bioreactor, f) minimizes heat delivery, and e) increases the overall sunlight utilization efficiency and cost-effectiveness when compared to earlier photobioreactors.

Figures 11, 12:
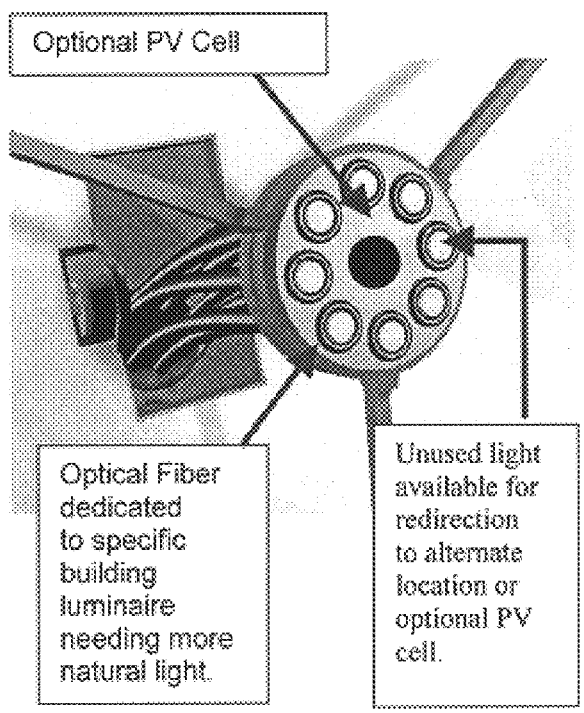
FIG. 11 is the concentric fiber mount assembly.
FIG. 12 is a table of the AFS system performance.

To make the above system adaptive, that is, able to respond to time-varying factors affecting its overall efficiency, this "intelligent" solar energy system adapts in real-time and continually optimizes solar energy utilization by using a lighting control system. For example, as lights are turned on and off or dimmed inside of buildings because of changing occupant needs or more visible light is available over and beyond what is needed for illuminating a certain region of a building or photobioreactor, the adaptive system redirects more visible light to other areas requiring illumination or possibly an alternative solar cell ideally-suited for energy conversion in the visible portion of the spectrum, see FIG. 11.

Figure 13:
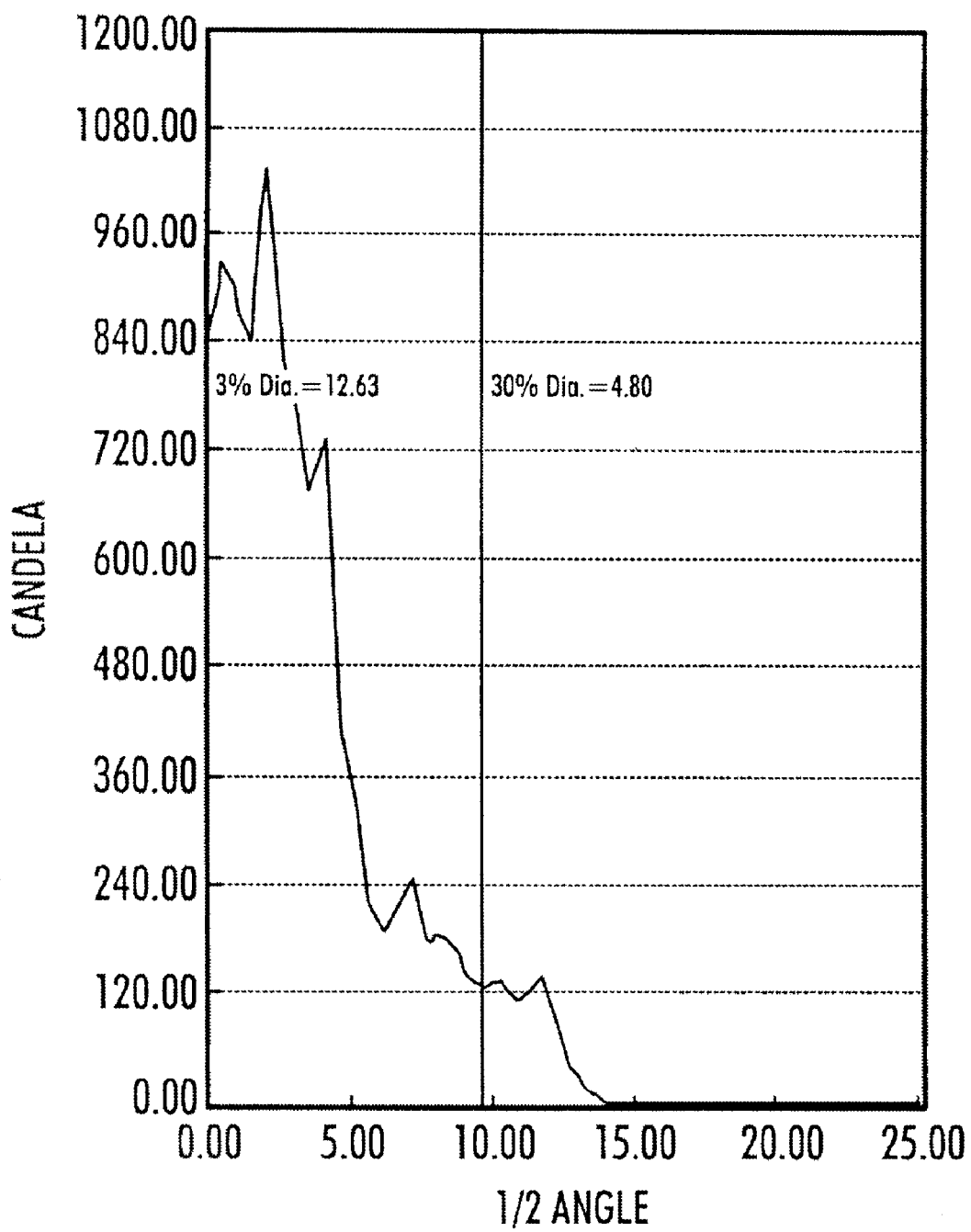
FIG. 13 is a graph of the results of initial optical analysis showing incident angles of light entering large-core optical fibers.

Light collection and delivery losses in the AFS system will be approximately 50% (see FIG. 12) for a single-story application and an additional 15% for second-story applications. These loss factors take into account losses attributed to the primary mirror, secondary UV cold mirror, large-core optical fibers (including bends), luminaires, and preliminary estimates for debris build-up and aging of the various optical components. The single largest contributor of loss is the large-core optical fibers. FIG. 9 graphs the attenuation of the fibers as a function of incident angle. Note that attenuation is strongly dependent in incident angle. Optical analyses of the invention indicate light will enter the fibers at an average incident angle of well under 10 degrees, as shown in FIG. 13. This represents one of several advantages of the AFS system when compared to earlier fresnel-based designs. Further, the fibers are solid-filled rather than a fiber optic bundle. As such, packing fraction losses are eliminated. Also, the luminaire efficacy of fiber-based systems is much better than traditional lamp/luminaire combinations (85% -vs-70%) because the directional nature of delivered sunlight emerging from the fibers makes it much more easy to control than light from traditional lamps.

Figure 14:
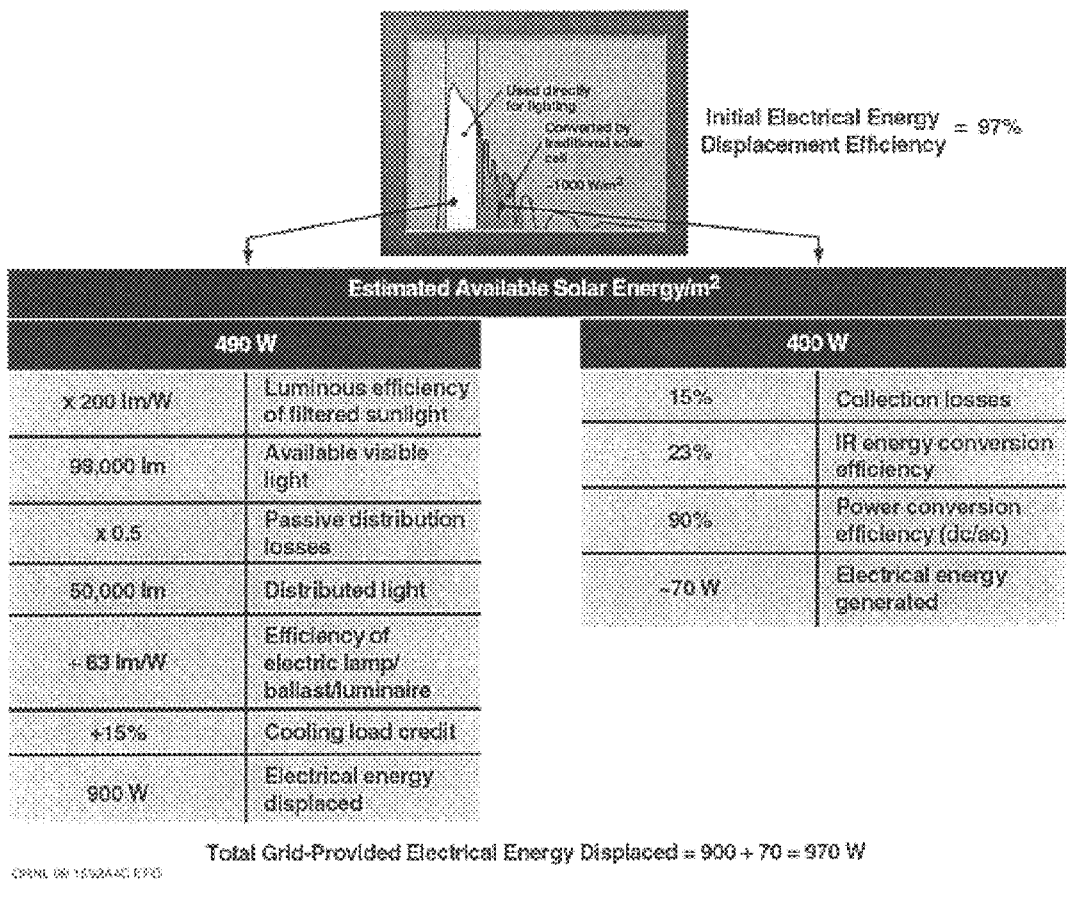
FIG. 14 is a summary table of full-spectrum solar energy system peak performance @ 1000 $W/m^2$ of incident solar power in commercial building.

Relative to the electrical energy displacement efficiency of the system, FIG. 14 summarizes the performance during peak use periods per 1000 $W/m^2$ of incoming solar flux. Note that the total electrical energy displacement efficiency is very close to 100%. In other words, 1000 W of collected sunlight displaces nearly an equal amount of electricity. At first glance, this might seem unreasonable. However, included in the performance summary are the following considerations: 1) the sunlight is filtered, the visible portion (~490 W) used for displacing much less efficient electric light (see FIG. 5) and the near-IR radiation (~400 W) used to generate electricity using ideally-sited IR-TPVs, 2) the luminous efficacy of the displaced electric light (63 lm/W) includes the luminous efficacy of the lamp/ballast (~90 lm/W) and the luminaire efficacy (70%); and 3) the elimination of excess heat generated by electric lights in sunbelt regions, which reduces subsequent HVAC loads by ~15%.

Optical losses in the sunlight collection/distribution system of this invention were recalculated for the hybrid solar photobioreactor. The results of this evaluation show that light collection and delivery losses in the AFS solar lighting system will be approximately 40% as compared to 50% for the top story of a commercial building. This is due to the fact that once inside the bioreactor, light losses along its length are desirable. Losses cause fibers to emit light (glow like a linear fluorescent lamp). The estimated photon flux rate that is effectively used to achieve maximum photosynthetic efficiency is therefore 1200 uEm$^2$s$^{-1}$.

Figure 15:
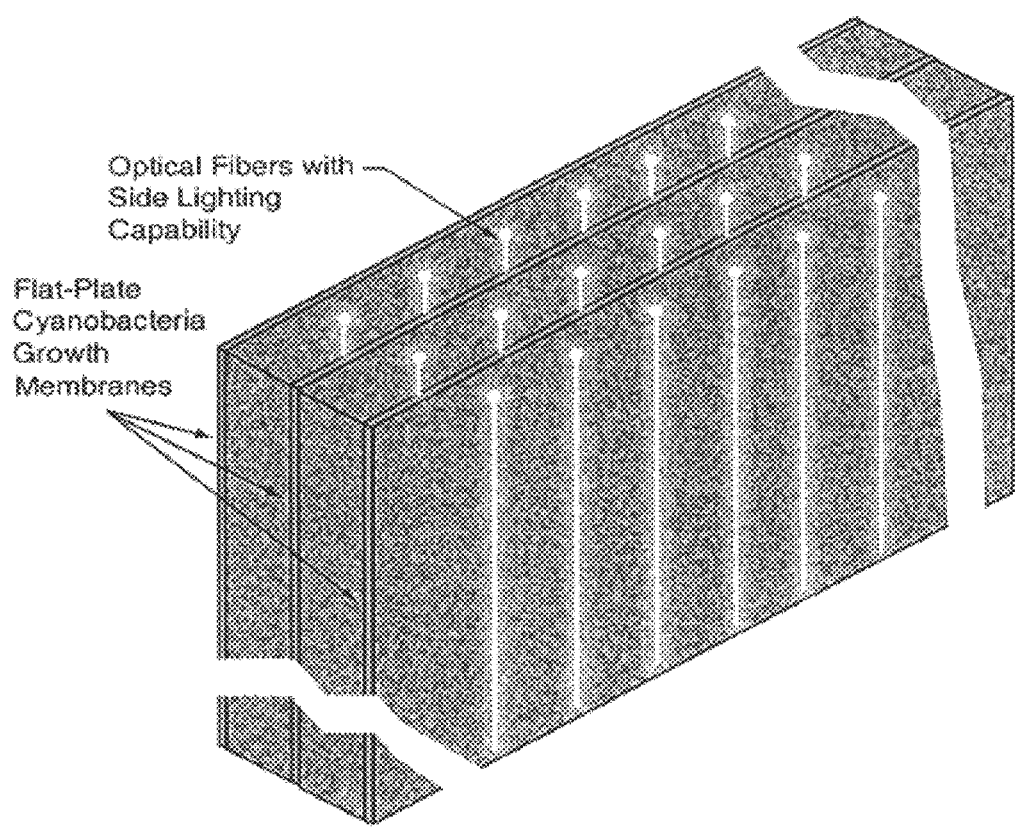
FIG. 15 the sidelighting design configuration for hybrid solar photobioreactor.

For mesophilic cyanobacteria whose preferred photosynthetic flux rate is 60 uEm$^2$s$^{-1}$, approximately 15 large-core fibers 5 mm in diameter, 6 m in length, and spaced 20 cm apart will deliver adequate lighting to achieve the desired spatial redistribution of 1 m$^2$ of direct sunlight into ~20 m$^2$ of vertically-stacked enclosed cyanobacteria growth area, i.e. $(0.60)(2000$ uEm$^2$s$^{-1})/20$ m$^2$=60 uEs$^{-1}$. FIG. 15 illustrates an example of how this sidelighting configuration is used to illuminate cyanobacteria surfaces spaced 15 cm apart.

Compared to earlier light collection systems developed by Himawara Corp. for solar lighting applications in buildings and photobioreactors, the AFS hybrid concentrator design provides several advantages: 1. fewer, easily assembled, system components integrated into a smaller, less costly, and more compact design configuration; 2. improved IR heat removal and management; 3.improved optical fiber placement and articulation (bundled and pivoted about a radial axis); 4. a longer optical path for light and lower entrance angles for visible light entering large-core optical fibers. This results in much lower overall transmission losses in the accompanying light delivery system (see FIG. 9); 5. centrally-concentrated IR radiation, allowing for convenient implementation of IR-TPVs.

Table 3 compares the projected cost and performance of the AFS system with that of a state-of-the-art commercial system. Accordingly, the anticipated cost per delivered lumen of the AFS system far exceeds its only commercial counterpart.

TABLE 3

| Parameter | AFS System | Commercial System |
|---|---|---|
| System Cost | $2000/m$^2$ | $5000/m$^2$ |
| Delivered lumens (buildings) | 50,000/m$^2$ | 25,000/m$^2$ |
| Delivered lumens (photobioreactors) | 60,000/m$^2$ | 25,000/m$^2$ |
| $/delivered lumen(buildings) | $0.04/lm | $0.20/lm |
| $/delivered lumen(photobioreactor) | $0.03/lm | $0.20/lm |

Skylights are generally accepted as the most cost-effective form of conventional topside daylighting. On average, incident sunlight does not enter skylights normal to the horizontal plane. Depending on the type and configuration of skylight, light transmission varies dramatically and is attenuated significantly. This is due to several factors but is predominately determined by the efficiency of the light well and glare control media. The typical transmittance of state-of-the-art tubular, domed skylights varies widely, depending on lighting requirements, but for commercial applications is typically well under 50%.

The coefficient of utilization (CU) of a single 1-m$^2$ tubular skylight will inherently be much lower than a system that distributes light from the same square meter to six or more luminaires. Assuming that the room cavity ratio and other room parameters are identical, the CU of the more distributed hybrid system is significantly better. If the single 1-m$^2$ skylight were replaced by ~6 much smaller skylights, the two systems CUs would compare equally, yet the cost of the skylights would increase prohibitively.

Skylights are typically not designed based on the maximum amount of light that can be supplied but rather designed to approximate that which is produced by the electric lighting system when the total exterior illuminance is 3000 footcandles. This reduces over-illumination and glare. Because of this, all light produced by skylights beyond this value is typically wasted. As such, preliminary estimates suggest that on average, depending on location, approximately 30% of the total visible light emerging from skylights on a sunny day is excess light not used to displace electric lighting. Conventional skylights are also plagued by problems associated with heat gain and do not harvest non-visible light. Finally, conventional skylights are not easily reconfigured during floor-space renovations common in today"s commercial marketplace. Once all factors are considered, the simple payback (typically >8 years) and energy end-use efficiency of even the best topside daylighting systems is considerably worse than projected adaptive, full spectrum solar energy systems.

Commercial solid-state semiconductor PV modules typically have a total conversion efficiency of <15%. Solar thermal systems typically have a conversion efficiency somewhat higher (<25%), depending on system design and complexity. Further, losses attributed to electric power transmission/distribution (~8%) and dc-ac power conversion (10–15%) further reduce the overall efficacy of conventional solar technologies. Because of these and other reasons, conventional solar technologies have not displaced significant quantities of nonrenewable energy and are expected to be used in the United States for residential and commercial buildings, peak power shaving, and intermediate daytime load reduction. The PV modules currently sell for between $3–$5/Wp. The projected peak performance of adaptive full spectrum (AFS) solar energy systems ($3,200 per 1,940 Wp or $1.65/Wp) have the immediate potential to more than double the affordability of solar energy when compared to these solar technologies.

Calculations based on earlier studies by Hirata et al. and Ohtaguchi et al. indicated that a little more than 1,000,000 m$^2$ bioreactor surface is required to reduce the $CO_2$ emission of a typical 500 MW coal-fired generation unit by 25%. This translates into 257 acres of water surface area for a high-density raceway type reactor. Using the design of Bayless et al., incorporating the novel solar collection technology described herein, the required area decreases to 11.7 acres. In a more practical scenario that considers roof-top collector/receiver packing densities and other factors, the required space would likely increase to 15 acres. An enclosed reactor of this size may be formidable to site and construct, but is certainly manageable compared to siting and operating a 257-acre pond near a power plant, which would create numerous groundwater contamination concerns. Further, an enclosed reactor has a number of options for delivery of the $CO_2$, including as raw flue gas. Bubbling flue gas through a 257 acre pond would be illegal, as the ground level contamination would be pose extreme health threats to the area. Therefore, a raceway reactor would require $CO_2$ separation before utilization, eliminating virtually any energy advantage of a bioreactor in $CO_2$ control.

Compared to previous attempts to develop similar solar-enhanced photobioreactors incorporating fresnel lenses and fiber optic bundles, the anticipated cost per delivered lumen (2.8 cents vs- 20 cents) also represents a seven-fold improvement in the cost of sunlight utilization not including the added benefit of electrical power generation. Thus, the primary advantages are enhanced sunlight utilization and less power consumption.

Non-photosynthetic carbon sequestration is a significant net energy loss. Separation of $CO_2$ from the flue gas either requires refrigeration or mechanical action. The sequestration (compression or pumping) of the separated $CO_2$ also requires significant energy. All totaled, $CO_2$ sequestration by non-photosynthetic means will require 25–40% of the power generated by a host utility compared to 2–5% for the hybrid solar photobioreactor. That means more fossil fuel will have to be burned to produce the same net power output before sequestration. This also has direct implications on the environment. Because more fuel must be burned to power the sequestration systems, more associated pollutants will be released, including ozone forming $NO_x$, mercury, PM.2.5 and other particulates. Only a system utilizing solar energy to produce biomass, as described in this invention, will require minimal power generation to minimize $CO_2$ emissions and does not produce significant harmful emissions.

Separation and use of different portions of the solar spectrum for different purposes improves the overall cost and performance of solar energy used at power plants. In addition to this advantage, biomass has inherent value beyond that of carbon sequestration. It can be used as a feedstock, agricultural supplement, food supplement, or in pharmacological uses. Third, coal must remain a viable fuel to maintain fuel diversity. Without coal, the long term (20+ years) price of electrical power will escalate at a dangerous rate, especially with regards to national economic growth. This system provides a critical component in the portfolio of carbon management techniques that will allow coal to remain viable.

The following references contain material relevant to this invention and are hereby incorporated by reference in their entirety:
1. National Laboratory Directors for the U.S. Department of Energy, "Technology Opportunities: to Reduce U.S. Greenhouse Gas Emissions, and "Technology Opportunities: to Reduce U.S. Greenhouse Gas Emissions: Appendix B; Technology Pathways," October 1997.
2. Barnes, F. A., et al., Electro-Optics Handbook: Technical Series EOH-11, RCA Corporation, 1974, p. 70.
3. Hanagata, N., Takeuchi, T., Fukuju, Y., Barnes, D., Karube, I., "Tolerance of Microalgae to High CO2 and High Temperature," Phytochemistry, Vol. 31(10), 1992, pp. 3345–3348.
4. Hirata, S., Hayashitani, M., Taya, M., and Tone, S. "Carbon Dioxide Fixation in Batch Culture of Chlorella sp. Using a Photobioreactor with a Sunlight Collection Device," Journal of Fermentation and Bioengineering, Vol.81, 1996, pp.470–472.
5. Ohtaguchi, K., Kajiwara, S., Mustaqim, D., Takahashi, N., "Cyanobacterial Bioconversion of Carbon Dioxide for Fuel Productions," Energy Conversion and Management, Vol.38 (Supplemental Issue), 1997, pp. 523–528.

What is claimed is:
1. An adaptive full spectrum solar energy system comprising:
   at least one hybrid solar concentrator, said solar concentrator further comprising;
      a fixed base,
      a rotating assembly,
      a rotational tracking mechanism operably connecting said fixed base to said rotating assembly, said rotating assembly further comprising;
         a primary mirror for producing reflected full spectrum solar radiation,
         a secondary optical element supported in position for receiving said reflected full spectrum solar radiation,
         a concentric fiber mount assembly operably mounted to said rotating assembly, and
         at least one optical fiber extending from said concentric fiber mount assembly to a light distribution system;
   at least one hybrid luminaire,
   at least one hybrid photobioreactor,
   said light distribution system operably connected to each of said hybrid solar concentrator, said hybrid luminaire, and said hybrid photobioreactor, and
   a means for controlling at least one of said hybrid solar concentrator, said hybrid luminaire, said hybrid photobioreactor, and said light distribution system.

2. The solar energy system of claim 1 wherein said hybrid luminaire comprises;
   at least one electric lamp,
   at least one large-core optical fiber operably connected to said light distribution system, and
   at least one light dispersing element fixably mounted in a lens diffuser.

3. The solar energy system of claim 2 wherein said hybrid luminaire further comprises;
   at least one cylindrical diffusing rod fixably aligned with said electric lamp.

4. The solar energy system of claim 1 wherein said secondary optical element further comprises;
   at least one secondary mirror for receiving said reflected full spectrum solar radiation and further reflecting only infrared filtered solar radiation,
   at least one nonimaging optic concentrator positioned for accepting infrared solar radiation transmitted through said secondary mirror, and
   at least one thermophotovoltaic cell positioned for accepting infrared solar radiation from said nonimaging optic concentrator.

5. The solar energy system of claim 1 wherein said optical fiber is large-core polymer construction.

6. The solar energy system of claim 4 wherein said secondary mirror further comprises a high temperature glass substrate with a sputtered ultraviolet cold coating on a first reflective surface.

7. The solar energy system of claim 4 wherein said secondary mirror further comprises segmented planar sections that precisely focus light into eight of the optical fibers.

8. The solar energy system of claim 4 wherein said secondary optical element further comprises an elliptical secondary element that extends the focus of said primary mirror and couples light into a packed array of nine of the optical fibers.

9. The solar energy system of claim 8 wherein the primary mirror is a low quality coated 1.5 m diameter hydroformed satellite dish.

* * * * *